United States Patent [19]

Khoobiar et al.

[11] Patent Number: 4,754,049

[45] Date of Patent: * Jun. 28, 1988

[54] PROCESS FOR PREPARING UNSATURATED NITRILES FROM ALKANES

[75] Inventors: Sargis Khoobiar, Kinnelon, N.J.; Arnold J. Shapiro, Bronx, N.Y.

[73] Assignee: Atlantic Richfield Company, Los Angeles, Calif.

[*] Notice: The portion of the term of this patent subsequent to Sep. 2, 2003 has been disclaimed.

[21] Appl. No.: 830,423

[22] Filed: Feb. 18, 1986

Related U.S. Application Data

[63] Continuation-in-part of Ser. No. 701,725, Feb. 14, 1985, Pat. No. 4,609,502.

[51] Int. Cl.$^4$ ............................................. C07C 120/14
[52] U.S. Cl. ...................................... 558/320; 558/319
[58] Field of Search ................................ 558/319, 320

[56] References Cited

U.S. PATENT DOCUMENTS

| | | | |
|---|---|---|---|
| 3,161,670 | 12/1964 | Adams et al. | 260/465.3 |
| 3,365,482 | 1/1968 | Khoobiar | 260/465.3 |
| 3,433,823 | 3/1969 | McMahon et al. | 260/465.3 |
| 3,479,416 | 11/1969 | Tschopp et al. | 260/683 E |
| 3,784,483 | 1/1974 | Cichowski | 252/437 |
| 3,868,400 | 2/1975 | Norton | 260/464 |
| 3,998,867 | 12/1976 | Takenaka et al. | 260/465.3 |
| 4,005,985 | 2/1977 | Hutson, Jr. | 23/288 R |
| 4,010,188 | 3/1977 | Grasselli et al. | 260/465 C |
| 4,036,870 | 7/1977 | Castellion et al. | 260/465.3 |
| 4,144,277 | 3/1979 | Walker et al. | 260/666 A |
| 4,176,140 | 11/1979 | Bertus et al. | 585/629 |
| 4,609,502 | 9/1986 | Khoobiar et al. | 558/320 |

*Primary Examiner*—Joseph Paul Brust
*Attorney, Agent, or Firm*—John C. Martin, Jr.

[57] ABSTRACT

Unsaturated nitriles, particularly acrylonitrile or methacrylonitrile, are produced in a process which integrates dehydrogenation of an alkane, particularly propane or isobutane, to the corresponding olefin, followed by ammoxidation of the olefin in the dehydrogenation reactor effluent to the corresponding nitrile. After recovery of the nitrile product, the residual gases are processed to remove hydrogen, oxygen, and carbon oxides, after which the gases are recycled to the dehydrogenation reactor. By operating with relatively low conversion of olefin to nitrile in each pass, the overall efficiency of the process is improved despite the need to recirculate substantial amounts of unreacted hydrocarbons.

1 Claim, 3 Drawing Sheets

PROCESS FOR PREPARING UNSATURATED NITRILES FROM ALKANES

CROSS REFERENCE TO RELATED APPLICATION

This is a continuation-in-part of application 701,725, filed Feb. 14, 1985, now U.S. Pat. No. 4,609,502, issued 9-2-86.

PRIOR ART

This invention relates to the preparation of unsaturated nitriles from the corresponding alkanes, particularly acrylonitriles from propane and methacrylonitrile from isobutane.

While commercial plants ammoxidize propylene to acrylonitrile, many patents have been obtained on processes which employ propane as a feed. Representative of these are U.S. Pat. Nos. 3,365,482, 4,010,188 and 4,036,870. Such one-step processes are of less commercial interest since the yield of acrylonitrile from propane is lower than is usual with propylene, thus offsetting the advantages of the lower cost feed material.

A feed mixture of saturated and unsaturated $C_4$ compounds was used in U.S. Pat. No. 3,998,867, producing both methacrylonitrile and 1,3-butadiene simultaneously. Including n-butane is said to increase the yield of methacrylonitrile from isobutylene, while dehydrogenating the n-butene to butadiene. The effect of butanes in the feed was not reported.

In U.S. Pat. No. 3,433,823 alkanes are used as feedstocks for nitriles. Two separate catalysts are employed, one of which must be a vanadium phosphate. The patentees apparently intended to carry out oxidation and ammoxidation simultaneously.

The composition of the feed to an ammoxidation process may have an important effect, as indicated in U.S. Pat. No. 3,535,366, where adding a heat carrier gas, such as methane, ethane, and carbon dioxide, is shown to moderate the "hot spot" in the fixed bed ammoxidation of xylenes to terephthalonitrile.

Improved yield of nitriles was obtained by adding carbon monoxide to the reactants, according to U.S. Pat. No. 3,868,400.

An integrated two-step process for production of unsaturated nitriles from alkanes is suggested in U.S. Pat. No. 3,161,670, where it is shown that the presence of hydrogen formed by dehydrogenating propane to propylene was not detrimental to the subsequent ammoxidation of the propylene to acrylonitrile. The effect of unreacted propane and steam is not considered, nor is a recycle process discussed.

Disadvantages associated with processes which convert alkanes to nitriles have limited their use, even though alkanes are generally less expensive feedstocks than the corresponding olefins. An efficient process for producing nitriles from alkanes has been found by the present inventors, as will be seen from the following description.

SUMMARY OF THE INVENTION

In an improved process for preparing nitriles, the corresponding alkane is dehydrogenated to the olefin over a Group VIII noble metal catalyst in the presence of steam, after which oxygen and ammonia are added to the effluent of the dehydrogenation step and the mixture passed over an ammoxidation catalyst to produce the nitrile. The product is absorbed from the ammoxidation effluent by an aqueous stream and recovered. The nitrile-depleted effluent is processed to selectively oxidize the hydrogen produced by dehydrogenating the alkane and to separate the net production of carbon oxides, after which the depleted effluent stream containing unreacted alkane and olefin is returned to the dehydrogenation reactor.

The process is of particular interest in the preparation of acrylonitrile from propane via propylene or alternatively preparation of methacrylonitrile from isobutane. When propane is the feedstock the dehydrogenation step is fed with propane and steam in a mol ratio of about 1/0.1 to 1/10 and at a temperature of about 400°–700° C. and a pressure about 0.1–5 bar. An average of about 20–60% of the propane is converted per pass, with a selectivity to propylene of about 92–98%.

The ammoxidation step is operated at an outlet temperature of about 375°–550° C. and a pressure of about 0.1–10 bar. The conversion of propylene to acrylonitrile is about 30–80% for each pass, preferably about 40–75%, and the selectivity to acrylonitrile is about 80–90%. These conditions contrast with the conventional once-through processes, which convert about 93% of the propylene with a selectivity of about 73% to acrylonitrile. Similar conditions are used when isobutane is dehydrogenated to isobutylene and then ammoxidized to methacrylonitrile.

DESCRIPTION OF THE PREFERRED EMBODIMENTS

In the process of the invention, an alkane, especially propane or isobutane, is dehydrogenated to the corresponding olefin and thereafter, oxygen and ammonia are added to the effluent of the dehydrogenation reaction and the mixture passed over a suitable catalyst to prepare the corresponding nitrile.

Figure 1:
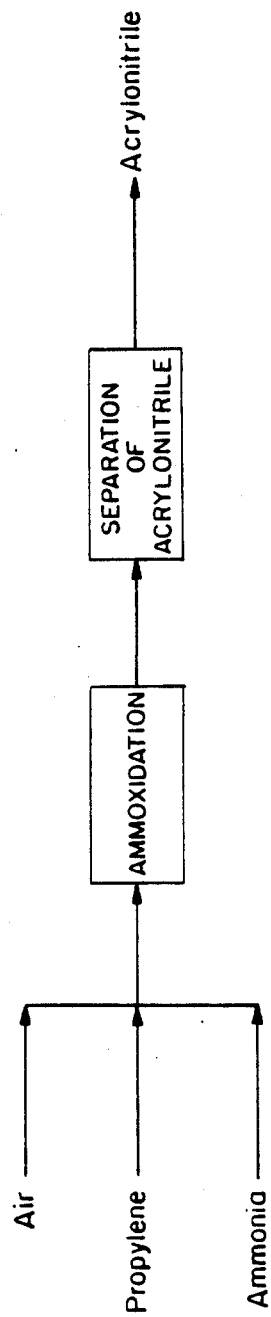
FIG. 1 illustrates in a block diagram a process of the prior art.

The block diagram of FIG. 1 illustrates the simplicity of the prior art process for making acrylonitrile from propylene. Propylene, air, and ammonia are fed to a catalytic reactor where a high yield of acrylonitrile is obtained. The product is recovered and purified by conventional absorption and distillation procedures. Since the yield of acrylonitrile is very high, any unconverted propylene may be disposed of. The analogous process for making methacrylonitrile from isobutane may also be carried out in a similar manner.

When one skilled in the art reviews the teaching of experts in the production of acrylonitrile, it becomes clear that, since the process is simple and the conversion is high, no incentive is seen for improvement—except possibly in the development of even more efficient catalysts. Generally, the catalysts used, such as antimony-uranium oxides, provide about 93% conversion of the propylene fed. Consequently, recycling to improve conversion of the propylene and selectivity to acrylonitrile is unattractive. One skilled in the art would conclude that recycling unreacted propylene would be technically feasible, but not cost effective since the raw material saved does not pay for costs of recycling.

If a skilled worker considered using propane as a feedstock, he would conclude that it is not cheap enough to justify the expense of dehydrogenating it to propylene, which is available at low cost as one of the products of steam-cracking naphtha or from natural gas liquids. If propane is used as a feedstock directly, as has been suggested in some patents, the yield of acrylonitrile is too low to provide an economical process. Since the commercial process is operated with high efficiency using propylene as a feedstock, propane would be seen as a less attractive choice.

The present inventors have found that the conventional wisdom outlined above leads to the wrong conclusions, and that propane can be efficiently converted to acrylonitrile. If propane is dehydrogenated to propylene and then fed along with ammonia to an acrylonitrile reactor, a substantial amount of propane remains. For efficient operation, a recycle of unconverted propane, which will be associated with any unconverted propylene, can be established to provide essentially complete conversion of the propane to acrylonitrile and byproducts. Then, if the conversion of propylene to acrylonitrile is kept unusually low, say, between 30 and 80%, so that the selectivity to acrylonitrile is higher than the usual 73%, for example, about 80-90%, the result is an efficient process, which, despite its complexity, is capable of low-cost production of acrylonitrile.

Figure 2:
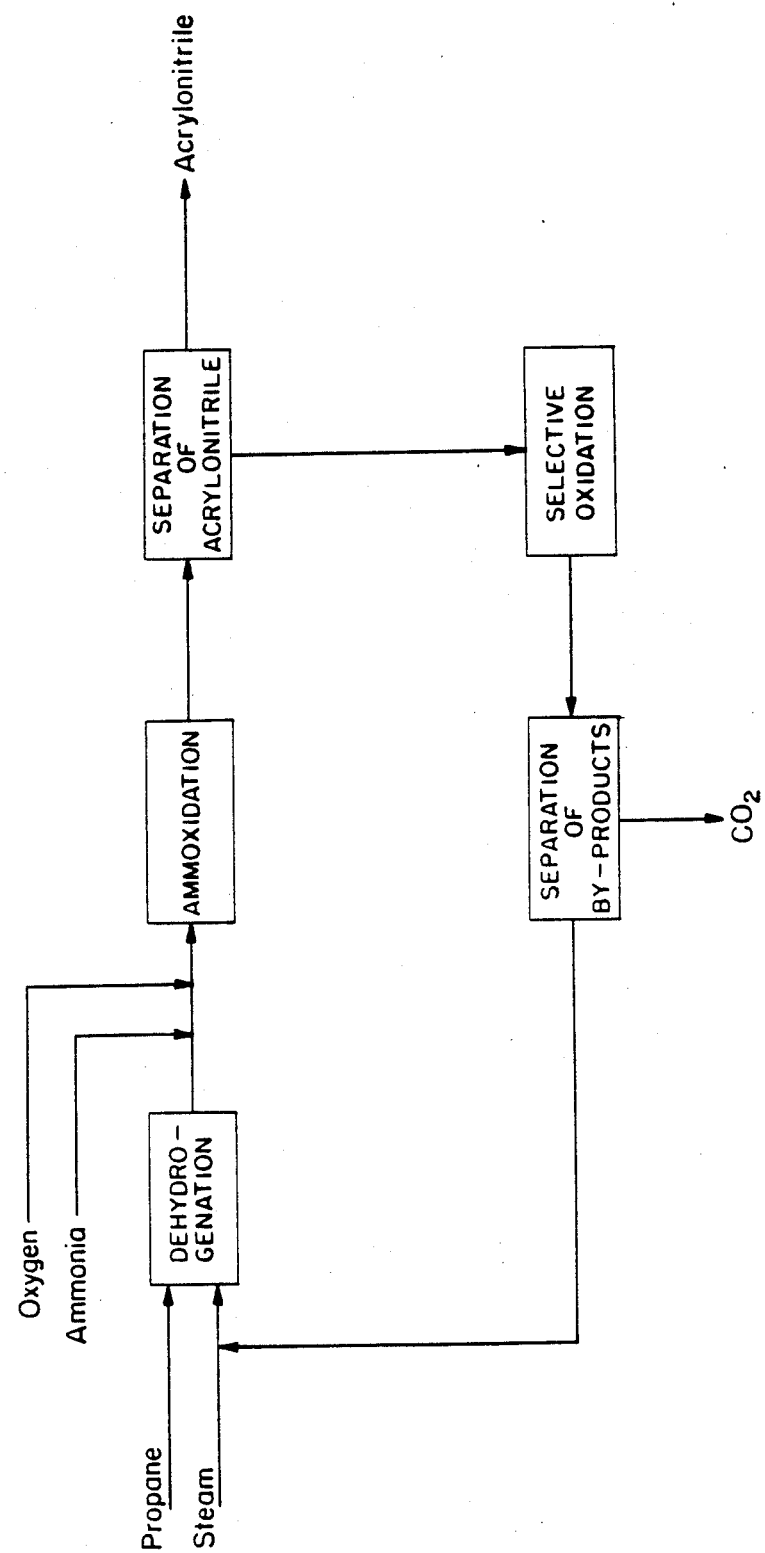
FIG. 2 illustrates in a block diagram the process of the invention.

Methacrylonitrile may be produced from isobutane in an analogous process. FIG. 2 generally illustrates such a process as applied to a propane feedstock. Propane and steam are fed to a dehydrogenation reactor where about 20-60% of the propane is converted to propylene, along with some byproducts, such as hydrogen, carbon oxides, methane, ethane, and ethylene. A substantial amount of propane remains unconverted, making it economical to recover and recycle it. The dehydrogenation takes place at conditions known in the art, that is, about 400°-700° C. and about 0.1-5 bar, over a supported Group VIII noble metal catalyst, usually including promoters. The reaction is quite endothermic, and more than one reactor may be used with reheating provided between them.

The dehydrogenation reactor effluent is fed directly to the ammoxidation reactor, along with added oxygen and ammonia. The steam content may be adjusted as desired. Again, the reaction is carried out at conditions known in the art, that is, temperatures of 375° to 550° C., pressures of about 0.1-10 bar, with ammonia to propylene mol ratios of 0.2/1 to 2/1. The catalyst may be any of those known in the art, but antimony-uranium compositions are preferred, employed either in a fixed-bed tubular reactor or in a fluidized bed reactor. It is characteristic of the process of the invention that, instead of obtaining the maximum yield of acrylonitrile in each pass through the ammoxidation reactor, the conversion is lowered from the maximum possible into the range of about 30 to 80%, preferably about 40-75%, while the selectivity to acrylonitrile becomes about 80 to 90%, depending upon the catalyst, its condition, and the operating conditions chosen. While operating under these unique conditions does increase the recycle of unreacted propane and propylene, it produces a larger net yeild of acrylonitrile for each mol of propane fed. This method has been found to provide more efficient production of acylonitrile than the simple once-through process of FIG. 1, despite being contrary to conclusions expected by those skilled in the art, as previously discussed.

Acrylonitrile is recovered and purified from the reactor effluent gases by conventional means. The residual gases include the unreacted propane and propylene, plus hydrogen, oxygen, carbon oxides, water, byproducts such as acetonitrile and hydrogen cyanide, and light hydrocarbons. The net hydrogen produced in dehydrogenating propane must be purged, along with carbon oxides. The residual oxygen cannot be returned to the dehydrogenation reactor, and it is selectively reacted with the hydrogen in a separate reactor over a catalyst capable of reacting hydrogen and oxygen without burning the propane and propylene. Such catalysts preferably are supported noble metals, such as platinum. The oxidation of hydrogen is carried out at suitable temperatures up to about 40°-550° C.

After the residual oxygen has been consumed by oxidizing hydrogen, sufficient gases will be purged to remove the net production of carbon oxides and light hydrocarbons. The purge gas is treated to recover the propane and propylene which it contains and is then disposed of. After removing the purge gases, the remainder of the effluent gases are recycled to the dehydrogenation reactor.

Where the process is applied to an isobutane feedstock, the same principles apply although the operating conditions will differ somewhat, as will be appreciated by those skilled in the art.

Figure 3:
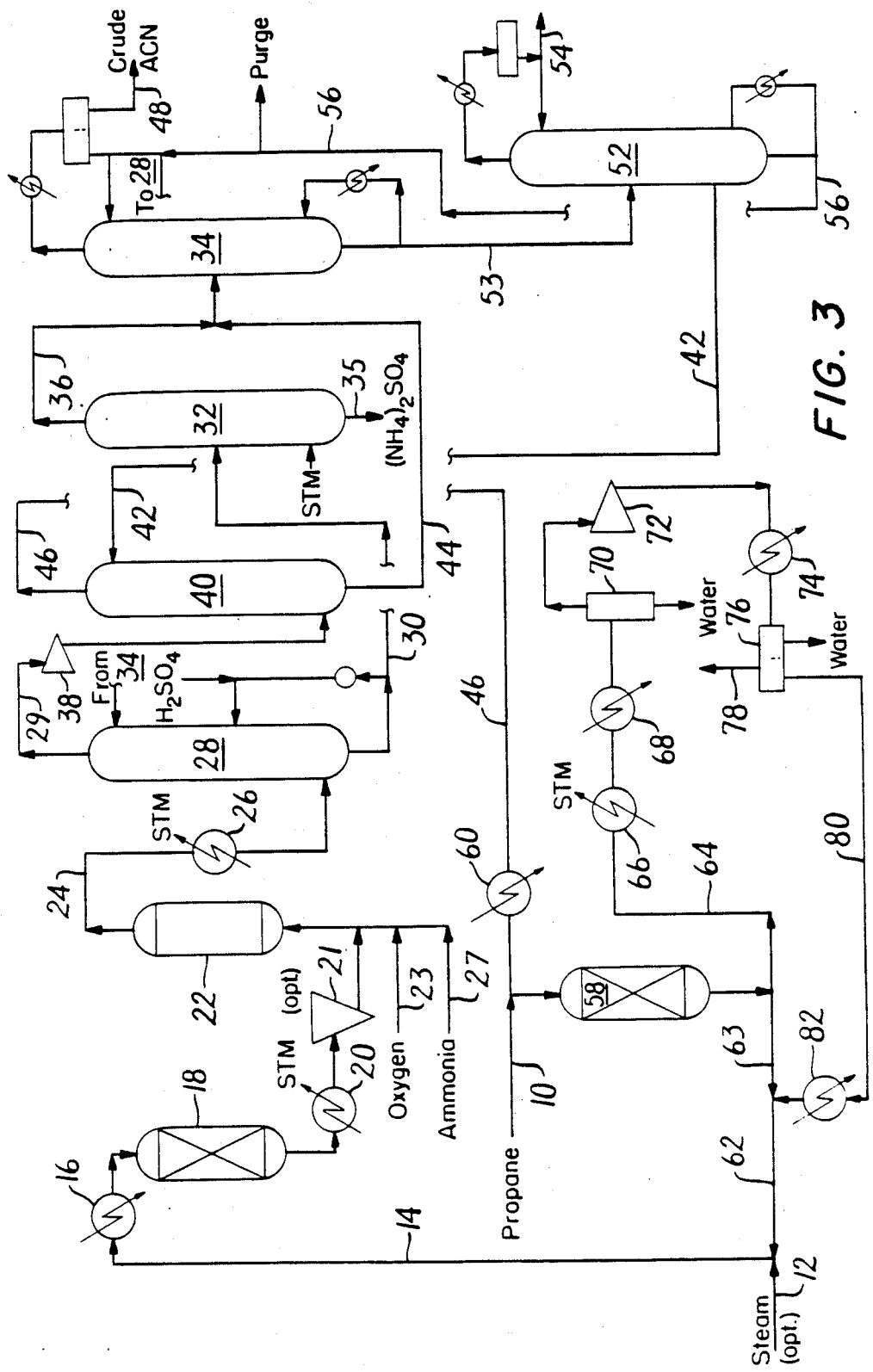
FIG. 3 provides a flowsheet showing one embodiment of the process illustrated in FIG. 2.

A simplified flowsheet is shown in FIG. 3 which will provide an example of a practical embodiment of the invention as it is a propane feedstock. Similar conditions would apply is isobutane were the feedstock. Fresh propane feed 10 is added upstream of selective oxidation reactor 58 to absorb some of the heat of reaction, and combined with recycle stream 46. The effluent of reactor 58 is sent to the dehydrogenation reactor 18 after a purge stream (64) is removed. The hydrocarbons recovered from purge stream 64 are returned via stream 80. The stream needed is supplied by the recycle gases, although additional steam (12) may be added if needed. The combined stream 14 is then heated in exchanger (or furnace) 16 to a temperature suited for the dehydrogenation of propane to propylene. The feedstream contains propane and steam in molar ratios between 1/0.1 and 1/10, preferably 1/0.2 to ¼, and is fed at temperatures between about 400°-700° C. preferably about 600° C., and at pressures about 0.1-5 bar, to reactor 18 where about 20-60% of the propane is converted to propylene with a selectively of 92-98%, depending upon the conditions chosen. The dehydrogenation reaction is endothermic, and the temperature leaving the reactor 18 will be lower than the inlet temperature. Multiple beds of catalyst with interstage heating of the gases may be used.

A number of catalysts have been disclosed in the prior art for use in this process, and the conditions under which the reaction is carried out will vary with the catalyst selected. Particularly useful is a platinum-based catalyst of the type shown in U.S. Pat. No. 4,005,985. Although platinum and tin disposed on a zinc aluminate support provide good performance, other catalysts which have been found effective include platinum and rhenium or indium supported on zinc aluminate. Other Group VIII noble metals, alone or in combination on various supports known to the art, may have application in the dehydrogenation of propane to propylene. Other potential supports would include alumina, other alkaline earth metal aluminates, and rare earth aluminates including lanthanum. Promoters such as tin, lead, antimony, and thallium may be used. Base metal catalysts, such as the chromium, zirconium, titanium, magnesium, and vanadium oxides shown in U.S. Pat. Nos. 3,479,416 and 3,784,483, or the zinc titanate of 4,176,140 and 4,144,277, also might be used. The invention is not considered to be limited to specific catalyst formulations.

It will be understood by those skilled in the art that this process involves a rapid deactivation of the catalyst, and typically the process will be operated with multiple reactors so that frequent regeneration is possible. The details of such operations are, however, not considered part of the invention.

The dehydrogenation reactor effluent is cooled by generating steam (20) to a suitable temperature for inlet to the ammoxidation reactor 22 and joined with oxygen (25) and ammonia (27) to provide a suitable feed for the ammoxidation of propylene to acrylonitrile. Substantially pure oxygen is preferred, although less pure oxygen could be used with a compensating increase in the purge gas removed. If the dehydrogenation reaction is operated at low pressures, a compressor (21) may be required. The reaction would be carried out under conditions typical of the art, that is, temperatures in the range of about 375°–550° C., pressures of about 0.1–10 bar. A suitable ammoxidation catalyst will be used, typically a mixture of base metal oxides, especially those which comprise antimony and uranium and include promoter elements. The reactor may be of the tubular type where the pelleted catalyst is placed inside tubes which are surrounded by a heat transfer fluid for the removal of the heat of reaction. Preferably, a fluid-bed reactor may be used. Typically, 30–80% of the propylene feed to the reactor will be converted to acrylonitrile, plus minor amounts of acetonitrile, hydrogen cyanide and light and heavier byproducts. A certain amount of the propylene is burned to carbon oxides and water.

The reactor effluent gases (24) may be cooled (26) by generating steam and fed to a quench tower 28 where any excess ammonia is reacted with sulfuric acid to form ammonium sulfate, which is scrubbed out at an aqueous stream. The aqueous ammonium sulfate (30) is steam-stripped in column 32 and removed as a bottoms product (35) including heavy byproducts. The overhead gases (36) which include some acrylonitrile, are sent of the acrylonitrile-acetonitrile splitter 34. Gases from the top of quench tower 28 are compressed (38) and sent to an absorber tower 40 where acrylonitrile is absorbed in a recirculating aqueous solution introduced as stream 42. The enriched solution passes as stream 44 to the acrylonitrile acetonitrile splitter 34. After the nitriles have been removed, the residual gases pass overhead from the absorber tower 40 as stream 46 for subsequent removal of oxygen and hydrogen and purge of carbon oxides.

The acrylonitrile-acetonitrile splitter 34 separates crude acrylonitrile as an overhead product (48) contaminated with byproduct hydrogen cyanide. The crude acrylonitrile is sent to a series of distillation columns for purification (not shown). The bottom product (53) is primarily acetonitrile containing high-boiling by products and water. The acetonitrile is purified by distillation in column 52, being taken as an overhead product (54). The recirculating aqueous stream used to absorb acrylonitrile is withdrawn from column 52 and sent to column 40 as stream 42. Heavy byproducts are purged from the bottoms stream 56 and the remainder is returned to the quench tower 28.

The effluent gas (stream 46) still contains significant quantities of hydrogen made in the dehydrogenation of propane and excess oxygen supplied to the ammoxidation reactor. The oxygen is removed from the effluent gas in oxidation reactor 58, which employs a catalyst capable of oxidizing hydrogen to water so that the $C_3$ components are substantially unaffected. Various oxidizing catalysts may be used for this purpose, such as noble metal or base metals. In particular, platinum or palladium on alumina has been found particularly useful, since the reaction can be initiated at near ambient temperature. However, any convenient temperature up to about 550° C. might be employed. Alternatively, platinum on a zeolite support sized to exclude $C_3$ hydrocarbons could be chosen. Such catalysts are capable of completely oxidizing hydrogen to water without oxidizing $C_3$ components. Thus, the effluent stream is adjusted to the desired reaction temperature by exchanger 60, fresh propane feed is added, and the mixture is passed over the selective oxidation catalyst (58) for removal of oxygen and hydrogen. After purging the net production of carbon oxides and light hydrocarbons, the remaining gases are passed to the dehydrogenation reactor 18 to repeat the process, as previously discussed.

Although oxygen has been removed, the gases still contain carbon oxides made during the ammoxidation reaction. Sufficient gas is purged via stream 64 to remove the net production of carbon oxides and light hydrocarbons. The purge gas is first cooled in exchangers 66 and 68, condensing water which is removed in knockout drum 70. The remaining gas is compressed (72), cooled (74), and separated (76). Waste gases are disposed of via stream 78, while water is purged from separator 76. The propane and propylene in the purge gas stream 64 are condensed in exchanger 74 and, being immiscible, are separated from the water inseparator 76. They are passed (80) to vaporizer 82 before being reintroduced into the recycle gas (62). Instead of the process just described, the $C_3$ content of the gases might be recovered by absorption in a suitable liquid. Also, carbon dioxide could be purged by absorbing it in an aqueous carbonate or other suitable solution.

An example of the practical operation of the flowsheet shown in FIG. 3 as applied to a propane feedstock is as follows:

One hundred mols/hr of a substantially pure propane feed stream (10) is vaporized and fed into stream 46 upstream of the selective oxidation reactor 58. Stream 46 totals 743 mols/hr and contains 14.9% hydrogen, 7.1% oxygen, 0.7% methane, 9.2% ethane, 6.9% propylene, 23.9% propane, 0.8% water, and 36.4% carbon oxides. The gas is sent at 60° C. to the selective oxidation reactor 58 where all of the oxygen is consumed. The water needed for dehydrogenation of the propane is supplied primarily by the selective oxidation of hydrogen, although some additional steam may be used. The effluent leaves at about 475° C., having been treated by combustion of hydrogen. Thereafter, the residual gases (about 790.5 mols/hr) are split and a purge stream of about 65.5 mols/hr is separated and about 95% of the $C_3$ content recovered and returned to the recycling gases (63). The carbon oxides, hydrogen, and other light gases are purged (78). This represents the net production of these gases which must be removed to maintain the material balance and will vary as reactor conditions change. About 73.5 mols/hr of steam are added (12) to stream 62 to complete the feed to the dehydrogenation reactor (18), totalling 798.4 mols/hr and comprising 1.3% hydrogen, 31.3% carbon oxides, 0.6% methane, 8% ethane, 6.3% propylene, 34.6% propane, and 17.6% water. The combined stream is fed to the dehydrogenation reactor 18 at about 600° C. and 0.7 bar, and over a platinum and tin on zinc aluminate catalyst about 35.7% of the propane fed is converted to propylene. Leaving the reactor at about 535° C., the effluent stream is cooled to about 150° C. in steam generator 20, compressed (21), and mixed with 214.5 mols/hr of oxygen (24) and 100.2 mols/hr ammonia before being supplied to the ammoxidation reactor 22, where over a catalyst about 65.7% of the propylene is converted to acrylonitrile. Leaving the reactor 22 at about 405° C. and 2 bar, the effluent gases are cooled to about 150° C. by generating steam and are passed to the quench tower 28 where the residual ammonia is neutralized by sulfuric acid and some water is removed. The remaining gases total about 1,208 mols/hr and contain 9.2% $H_2$, 4.3% $O_2$, 5.7% ethane, 4.2% propylene, 14.7% propane, 22.4% carbon oxides, 6.7% acrylonitrile, 0.5% acetonitrile, 1% HCN, 31% $H_2O$, plus minor amounts of various byproducts. This gas is compressed (38) and sent to the acrylonitrile absorber 40 where the product acrylonitrile is absorbed at about 40° C. and 6 bar in a recirculating aqueous stream (42) of about 4,128 mols/hr.

The aqueous stream containing acrylonitrile (44) is distilled in column 34 to produce a crude acrylonitrile stream (48) containing byproduct HCN, which is purified by subsequent distillation columns (not shown). Byproduct acetonitrile is separated from the aqueous absorbing liquid by distillation in column 52, with the aqueous stream being returned (42) to the absorber 40 for reuse.

Where isobutane is used as a feedstock, the operating conditions will be similar, as will be appreciated by one skilled in the art.

What is claimed is:

1. A process for the preparation of methacrylonitrile from isobutane comprising:
   (a) dehydrogenating isobutane to isobutylene in the presence of 0.01 to 10 mols of steam for each mol of isobutane, over a supported Group VIII noble metal dehydrogenation catalyst at a temperature of about 400°–700° C. and a pressure of about 0.1–5 bar to form an effluent stream comprising isobutylene, hydrogen, carbon oxides, steam, light hydrocarbons, and unreacted isobutane;
   (b) mixing oxygen and ammonia with said effluent stream of (a) and passing the mixture over an ammoxidation catalyst at a temperature of about 375°–550° C. and a pressure of about 0.1–10 bar selected to convert about 30–80% of said isobutylene with a selectivity to methacrylonitrile of about 80–90%, and producing an effluent stream comprising methacrylonitrile, unreacted isobutane and isobutylene, oxygen, hydrogen, steam, light hydrocarbons, and carbon oxides;
   (c) absorbing said methacrylonitrile from said effluent of (b) into an aqueous stream;
   (d) selectively oxidizing the hydrogen from the methacrylonitrile depleted effluent of (c) to water over a catalyst;
   (e) separating a portion of the effluent stream of (d) after said oxidation containing the net production of carbon oxides and light hydrocarbons, recovering the isobutane and isobutylene content thereof, purging the net production of carbon oxides and light hydrocarbons and returning said recovered isobutane and isobutylene to the dehydrogenation step of (a); and
   (f) returning the effluent stream (d) after the separation of a portion thereof in (e) as feed to the dehydrogenation step of (a).

* * * * *